United States Patent [19]

Dobbs et al.

[11] Patent Number: 5,781,606

[45] Date of Patent: *Jul. 14, 1998

[54] X-RAY TOMOGRAPHY SYSTEM WITH SUBSTANTIALLY CONTINUOUS RADIATION DETECTION ZONE

[75] Inventors: John Dobbs, Hamilton; Ruvin Deych, Burlington, both of Mass.

[73] Assignee: Analogic Corporation, Peabody, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 687,747

[22] Filed: Jul. 25, 1996

[51] Int. Cl.$^6$ .................................................. A61B 6/06
[52] U.S. Cl. ...................................... 378/19; 378/4
[58] Field of Search ................. 378/19, 4, 7; 250/367

[56] References Cited

U.S. PATENT DOCUMENTS

| | | |
|---|---|---|
| 4,338,521 | 7/1982 | Shaw et al. . |
| 4,417,354 | 11/1983 | Pfeiler ........................ 378/19 |
| 4,694,399 | 9/1987 | Tan et al. ................... 378/19 X |
| 4,755,681 | 7/1988 | Oka et al. .................... 250/367 |
| 5,025,462 | 6/1991 | Saito et al. . |
| 5,463,224 | 10/1995 | Burstein et al. . |
| 5,487,098 | 1/1996 | Dobbs et al. . |
| 5,493,593 | 2/1996 | Muller et al. ................. 378/19 |

*Primary Examiner*—David P. Porta
*Attorney, Agent, or Firm*—Lappin & Kusmer LLP

[57] ABSTRACT

In an x-ray scanning system having an x-ray source and an x-ray detector assembly, including a plurality of x-ray detector crystals grouped in substantially linear arrays and cooperative with the x-ray source, a substantially continuous radiation detection zone is established by positioning the detector arrays so that substantially all radiation from the source passing through the detector assembly passes through at least a portion of at least one detector crystal. The detector arrays are tilted at a preselected angle $\alpha$ with respect to a nominally perpendicular orientation relative to radial lines extending from the focal spot, so that the spaces between adjacent detector crystals in an array are not aligned with x-rays emanating from the x-ray source. The angle $\alpha$ is a function of the geometry of the detector crystals and the spaces between adjacent crystals in an array.

13 Claims, 3 Drawing Sheets

X-RAY TOMOGRAPHY SYSTEM WITH SUBSTANTIALLY CONTINUOUS RADIATION DETECTION ZONE

TECHNICAL FIELD

This invention relates generally to x-ray computed tomography (CT) systems, and more particularly to arrangements for x-ray detector assemblies within such systems.

BACKGROUND OF THE INVENTION

Third-generation CT scanners typically include an x-ray source and an array of x-ray detectors secured respectively on diametrically opposite sides of an annular disk, the latter being rotatably mounted within a gantry support. During a scan of a patient located within the opening of the disk, the disk rotates about a rotation axis while x-rays pass from the focal spot of the X-ray source through the patient to the detector system.

The x-ray source and detector array are positioned so that the x-ray paths between the focal spot and each detector all lie in the same plane (the so-called "slice plane", "rotation plane" or "scanning plane") which is normal to the rotation axis of the disk. Because the ray paths originate from substantially a point source and extend at different angles to the detectors, the ray paths resemble a fan, and thus the term "fan beam" is used to describe all of the ray paths at any one instant of time. The radiation that is detected by a single detector at a measuring instant during a scan is considered a "ray" or "beam". The ray is partially attenuated by the mass of the patient in its path and each detector generates a single intensity measurement as a function of the integral of the attenuation, and thus of the density of the portion of the patient in the path of the ray from the focal spot to that detector. These x-ray intensity measurements, or projections, are typically performed during prescribed measurement intervals at each of a plurality of angular disk positions.

Various types of detectors have been developed, including gas and solid state types. A typical solid state detector (hereinafter, "detector" or "detector channel") includes a scintillating crystal which converts high energy x-radiation photons into low energy visible light photons, and a photodiode which converts the low energy visible light photons into extremely low-amplitude electrical currents (i.e., on the order of picoamperes to nanoamperes). The output of each detector channel represents the x-ray flux incident on the detector crystal. The outputs of the detector array are transmitted via an array of conductors to a data acquisition system (DAS) for signal processing.

Because the resolution of the resulting image is a function of the size of the detectors, a CT scanner system typically includes hundreds of detectors which are extremely closely spaced along an arc extending about the focal spot. For reducing the costs of such detector arrays, the use of preassembled solid state detector modules, each comprising several solid state detectors, has been described in U.S. Pat. No. 5,487,098, issued to John Dobbs and David Banks and assigned to the present assignee. For example, one third-generation CT scanner system manufactured by the present assignee includes 384 detectors provided by 24 modules of 16 detectors each and closely spaced within an arc which subtends not more than 48 degrees. The width of a single detector is thus on the order of a millimeter.

The depth or height of a detector (i.e., its dimension in the radial direction) is determined by the conversion of x-ray photons to optical photons, which is a probabilistic function. The deeper the penetration of the x-rays into the crystal, the higher the percentage of conversion. Thus, in order to have a conversion of at least 99%, the height or depth of the detector in the radial direction is typically on the order of 2.5 millimeters.

Each detector in a module is typically surrounded on all sides by a highly optically reflective material. This material is substantially transparent to x-rays, yet it prevents excessive light leakage between crystals, thus substantially reducing or eliminating optical cross-talk between adjacent detector channels. In addition, the reflective material reflects visible light generated by a crystal onto the underlying photodiode, thereby increasing the signal level from that crystal. The presence of this highly reflective material between detector crystals effectively separates the crystals by a narrow region of relatively low sensitivity to radiation of at least 0.2–0.3 millimeters. The depth of this region is equal to the depth, in the radial direction, of the crystals, or about 2.5 millimeters.

A plot of the response of a detector crystal to radiation indicates a generally constant maximum sensitivity over the main, or central, portion of the detector crystal and a relatively steep drop to a region of lower sensitivity at the edges of the detector crystal, as well as between adjacent crystals in an array. The detection zone of a CT scanner system is made up of a plurality of discrete detecting regions (detector crystals) separated by regions of decreased sensitivity (reflective material) between individual detector crystals and between adjacent detector arrays.

For convenience in handling and in manufacturing, the detectors are typically grouped in generally linear arrays of at least 16, and sometimes 24, detectors per array. It is desirable to make the space between adjacent detector crystals which is relatively insensitive to radiation as small as possible in order to more closely simulate a continuous detecting region. However, it is difficult in practice to place the detectors close enough to obtain a truly continuous detecting region, because of the presence of the highly reflective coating between the detectors of an array, and because variations in the as-manufactured dimensions of the detector. The spaces between individual detector channels and between adjacent detector arrays are manifested as regions of diminished signal information in each projection of the patient. The existence of such regions diminishes the efficiency of radiation detection of the system and thus influences the accuracy and the resolution of the reconstructed image.

It would therefore be an advantage in the art of CT scanner systems to provide a system which overcomes the disadvantages of the present systems.

OBJECTS OF THE INVENTION

It is therefore an object of the present invention to provide an x-ray scanning system which has a substantially continuous radiation detecting zone.

It is another object of the invention to provide an x-ray scanning system in which the detector placement is optimized for maximum geometric efficiency.

It is yet another object of the invention to provide an x-ray scanning system in which the existence of gaps between adjacent detector crystals of an array and between adjacent arrays does not diminish the efficiency of radiation detection of the system.

SUMMARY OF THE INVENTION

An x-ray scanning system according to the invention includes (a) an x-ray source for defining a focal spot from which a beam of radiation is emitted, (b) a structure for supporting the x-ray source for rotation about a rotation axis, and (c) an x-ray detector assembly including a plurality of x-ray detectors arranged in an array and cooperative with the x-ray source so as to define the beam of radiation from the focal spot to all of the detectors. The x-ray scanning system further comprises means for positioning the detectors relative to the focal spot and to one another so as to establish a substantially continuous radiation detection zone within the beam of radiation. According to the invention, substantially all radiation within the beam passing through the array passes through at least a portion of at least one detector.

The detectors are grouped in substantially linear arrays which are oriented so that the narrow spaces between adjacent detectors in an array are not aligned with radial lines extending from the focal spot, and thus not aligned with radiation beams emanating from the x-ray source. The arrays are thus not perpendicular to such radial lines but instead are oriented at a preselected angle α with respect to a nominally perpendicular orientation of the arrays relative to radial lines extending from the focal spot to approximately the centers of the arrays. The value of the angle α is a function of the geometry of the detector crystals and the spacing between the crystals and is selected to permit substantially all of the radiation emitted from the source and impinging on a detector to pass through at least a portion of at least one detector crystal.

Each detector array is preferably a modular unit which is adapted for engagement with the support structure.

The x-ray scanning system of the invention can further include an anti-scatter plate assembly mounted on the support structure and including a plurality of anti-scatter plates disposed between the x-ray source and the detector assembly. The anti-scatter plates, which are substantially aligned with radial lines extending from the focal spot, are preferably positioned so that they are also substantially aligned with the regions of constant maximum sensitivity of corresponding detectors.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

DETAILED DESCRIPTION OF THE DRAWINGS

The term "radial", as used herein, refers to a direction from or toward the focal spot of the x-ray source. The term "tangential", as used herein, refers to a direction substantially perpendicular to the radial direction and substantially perpendicular to the axis of rotation of the x-ray scanner.

The CT scanner system of the present invention provides a substantially continuous radiation detection zone by providing means for orienting all of the detector arrays so that the spaces between adjacent crystals of an array are not aligned with radial lines extending from the focal spot and thus are not aligned with x-rays emanating from the focal spot. The arrays are instead oriented at a preselected angle α relative to a nominally perpendicular orientation of the arrays with respect to radial lines extending from the focal spot to approximately the centers of the arrays. The angle at which the arrays are oriented is selected to permit substantially all the radiation emitted from the source and impinging on the detector assembly to pass through at least a portion of at least one detector crystal. The value of the angle α depends on the geometry of the detector crystals and the spaces between them, and specifically on the height of the detector crystals, as measured in the radial direction, and the width of the spaces between the crystals, as measured in the tangential direction. As a result of this tilting of the detector arrays away from a nominally perpendicular orientation, substantially all of the radiation from the x-ray source and passing through the detector assembly impinges on at least a portion of at least one detector crystal, and virtually no radiation impinges solely on a region of relatively low sensitivity to radiation between detector crystals or between detector arrays.

Figure 1:
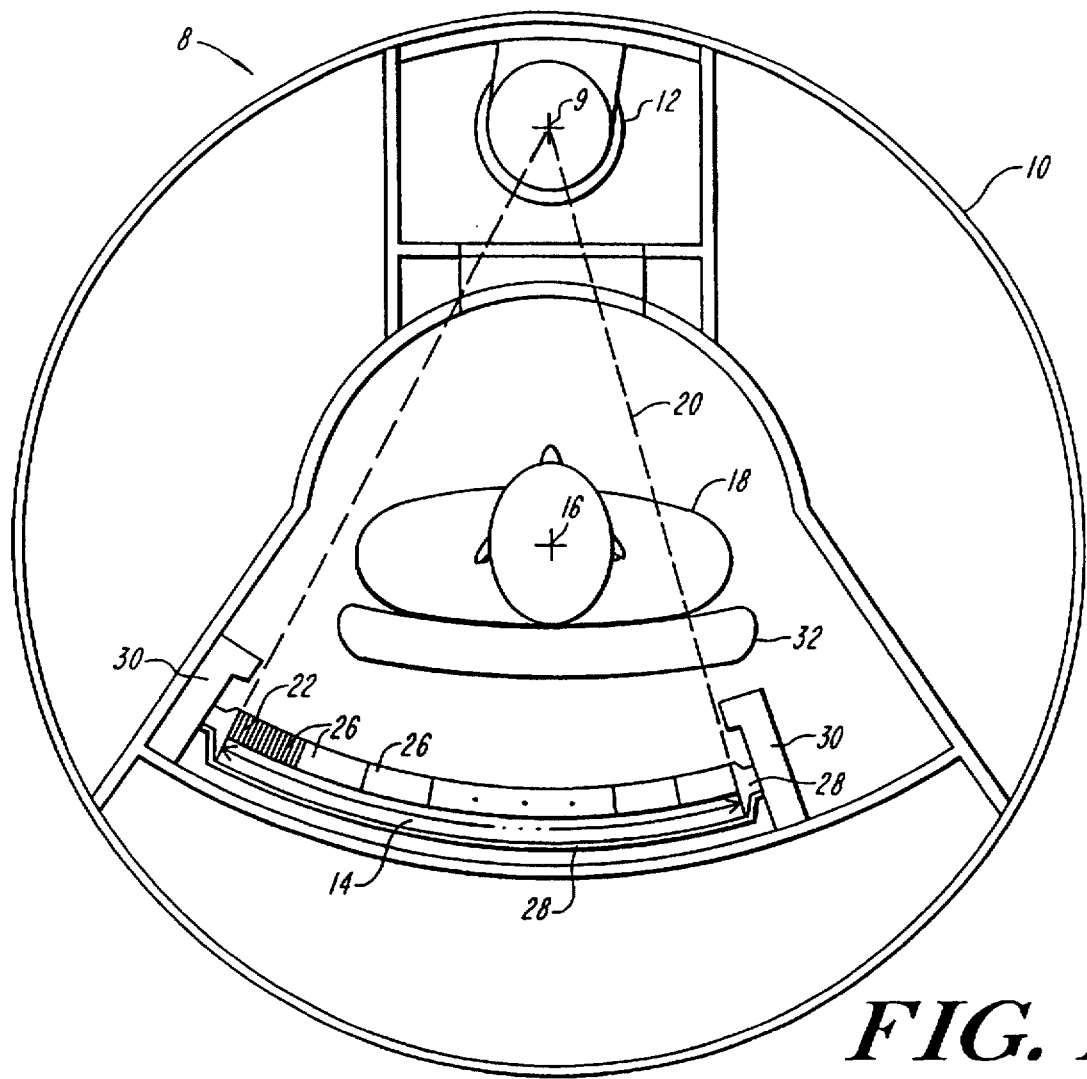
FIG. 1 is an axial view of a CT scanner system according to the present invention.

FIG. 1 represents a CT scanner system according to the present invention. To provide the data for a CT scan, scanner 8 includes a source 12 of x-rays and a detector assembly 14 mounted to a disk 10. Source 12 and detector assembly 14 are rotated about a rotation axis 16 (extending normal to the view shown in FIG. 1) so as to rotate around the object 18 that extends through the central opening of the disk during the CT scan. Object 18 may be a part of a live human patient, such as the head or torso. Source 12 emits within the scanning plane (normal to rotation axis 16) a continuous fan-shaped beam 20 of x-rays, which emanates from a focal spot 9 and extends to and is sensed by the detectors of assembly 14 after passing through object 18. An array of anti-scatter plates 22 is located between object 18 and the detectors of assembly 14 to substantially reduce the amount of scattered radiation sensed by the detectors.

In the preferred embodiment the detectors number 384 and cover an arc of 48°, although the number and angle can vary. Referring again to FIG. 1, disk 10, which may advantageously be of a lightweight material, such as aluminum, is caused to rotate rapidly and smoothly around axis 16. The disk 10 is of an open frame construction so that object 18 can be positioned through the opening of the disk. Object 18 may be supported, for example, on a pallet or table 32, which should be as transparent as practical to x-rays. As disk 10 rotates, detectors of assembly 14 are periodically sampled to provide discrete measurements of x-rays passing in the scanning plane through object 18 from many projection angles. The measurements are then processed electronically with appropriate signal processing equipment (not shown), in accordance with well-known mathematical techniques, so as to produce the final image information. The image information may then be placed in memory, analyzed in a computer, or suitably displayed.

The detector assembly 14 includes a base support element in the form of a supporting spine 28. The detectors and anti-scatter plates are each assembled into a plurality of identical respective modules 24 and 26. The modules are then accurately aligned and secured to the spine 28, and the spine supported by disk 10 with suitable supports 30 so that the detectors all lie in the scanning plane and subtend an equal angle with respect to the focal spot 9 of the x-ray source 12.

Figure 2:
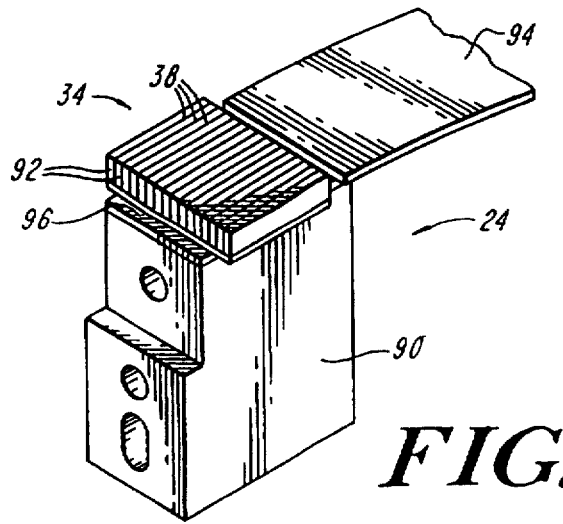
FIG. 2 is a perspective view of a preferred embodiment of a detector module according to the present invention.

A preferred form of the detector module 24 is shown in detail in FIG. 2. This module comprises a metal block 90 with an array 34 of solid state detectors 92 and a multi-conductor ribbon cable 94, or other flexible connector, mounted on one face thereof. At least a portion of block 90 is preferably narrower than the array 34, to facilitate close placement of the detector arrays without interference of the blocks with one another. In the illustrated embodiment, the width of the block 90 is uniformly less than the width of the array 34; however, other configurations which facilitate placement of the arrays to maximize geometric efficiency and minimize the probability that radiation will impinge on a region of low sensitivity to radiation between detector crystals, are within the scope of the present invention.

Although the photodiode underlying the detector array can detect some radiation which impinges on the region of reflective material between adjacent detector crystals, the detection by the photodiode is significantly attenuated, such that only about 1% of the radiation is detected. Thus, it is desirable to avoid direct impingement of radiation on the spaces between the detector crystals.

Figure 3:
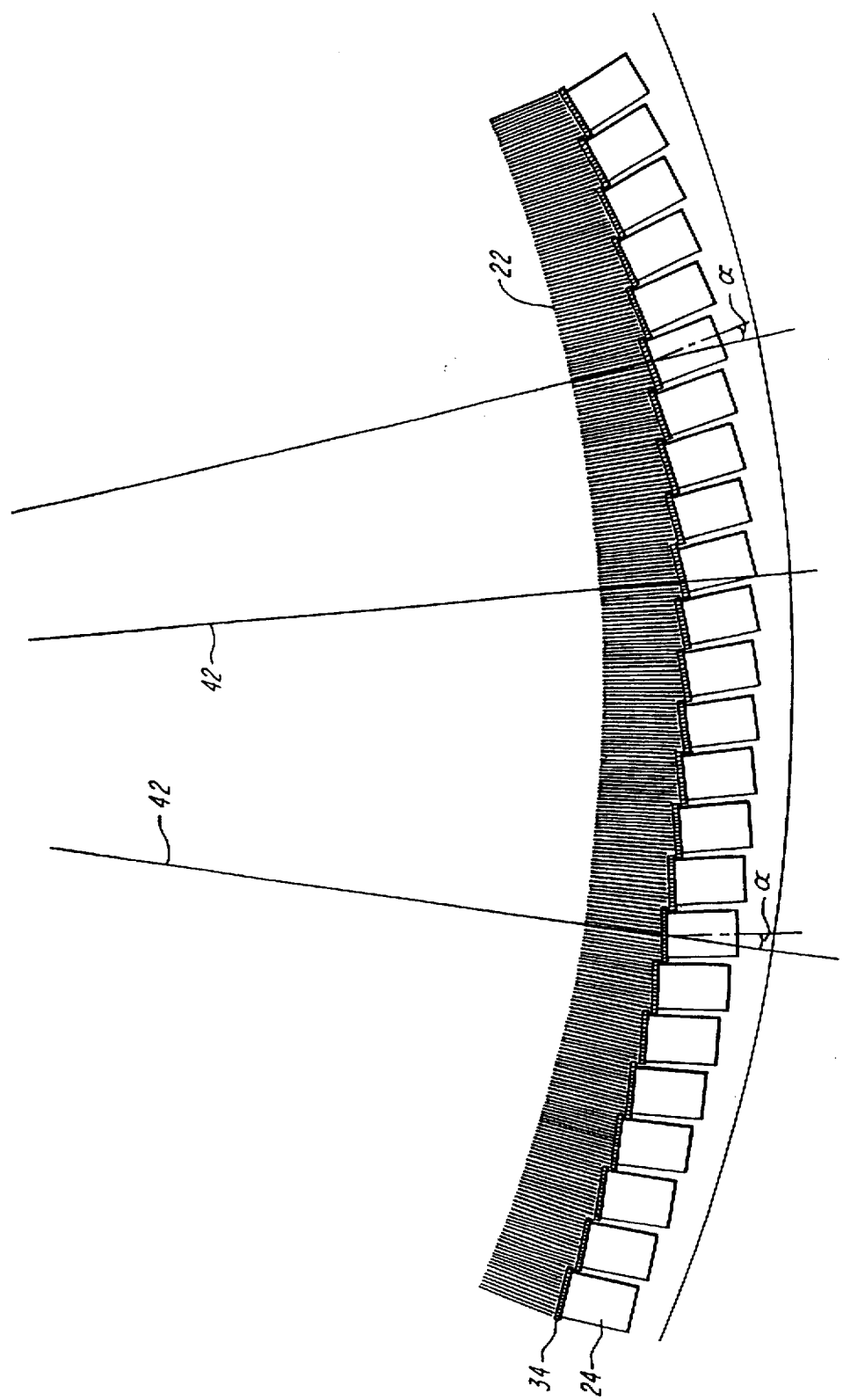
FIG. 3 is a simplified axial view of a portion of a CT scanner system according to a preferred embodiment of the invention.
Figure 4:
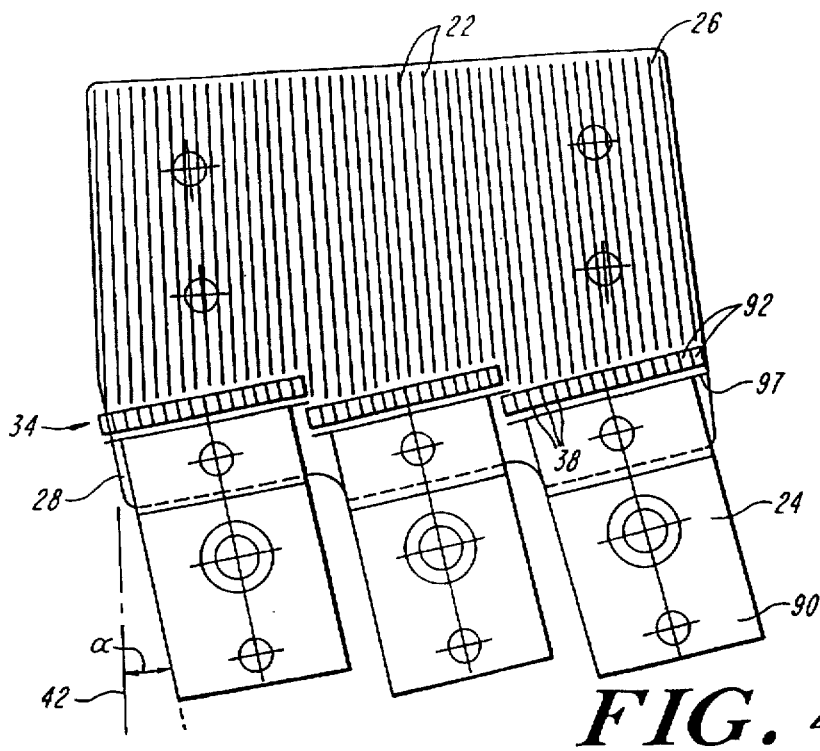
FIG. 4 is a simplified plan view of the modular detector and anti-scatter plate assemblies on the support structure according to a preferred embodiment of the invention.

A CT scanner system employing a preferred embodiment of the detector module arrangement of the present invention is illustrated in FIGS. 3 and 4. Sixteen detector crystals 92 are mounted in a linear array 34 on a modular block 90. As shown more clearly in FIG. 4, the array 34 extends beyond the edges of the block 90 so that the detector crystals of adjacent arrays can be closely spaced in the tangential direction along the fan beam arc without interfering contact between the ends of an array and the block of an adjacent detector module. Each of the detector modules 24 is tilted by a preselected angle α relative to a nominally perpendicular orientation of the array relative to a radial line 42 extending from the focal spot 9 (not shown) to the center of the array. By imparting a tilt to the detector arrays 34, they can be arranged in a tangentially overlapping, or "fish scale", pattern so that the spaces between adjacent detector crystals (designated as regions of reflective material 38) are not aligned along radial lines 42. In addition, the extent of the overlap of adjacent detector arrays can be adjusted so that all of the radiation emanating from the focal spot and directed toward those detector modules passes through at least a portion of at least one detector crystal. As a result, x-rays from the x-ray source impinge on at least a portion of at least one detector crystal and not solely on the regions of reflective material between detector crystals.

To preclude the impingement of stray or scattered radiation on the detector crystals, particularly from the irradiation of dense matter, an array of elongated, thin "anti-scatter" plates 22 is positioned between the x-ray source and the detectors. The anti-scatter plates are opaque to x-rays and are aligned relative to the detectors so as to permit passage of substantially only those rays traversing a straight line from the source to a detector. The anti-scatter plates are generally placed so that they are aligned along radial lines 42 extending from the focal spot, and they are positioned so that they block any rays that impinge on the detector crystal at an angle which varies, for example, by more than about three degrees from a normally incident ray along the respective ray path.

FIG. 4 illustrates a portion of the CT scanner system according to a preferred embodiment of the present invention, in which the detector modules 24 and anti-scatter plate modules 26 are mounted on a support structure, or spine, 28. The anti-scatter plate modules 26 are positioned and secured relative to the detector modules 24 so that the anti-scatter plates 22 are substantially aligned with radial lines extending from the focal spot.

Figure 5:
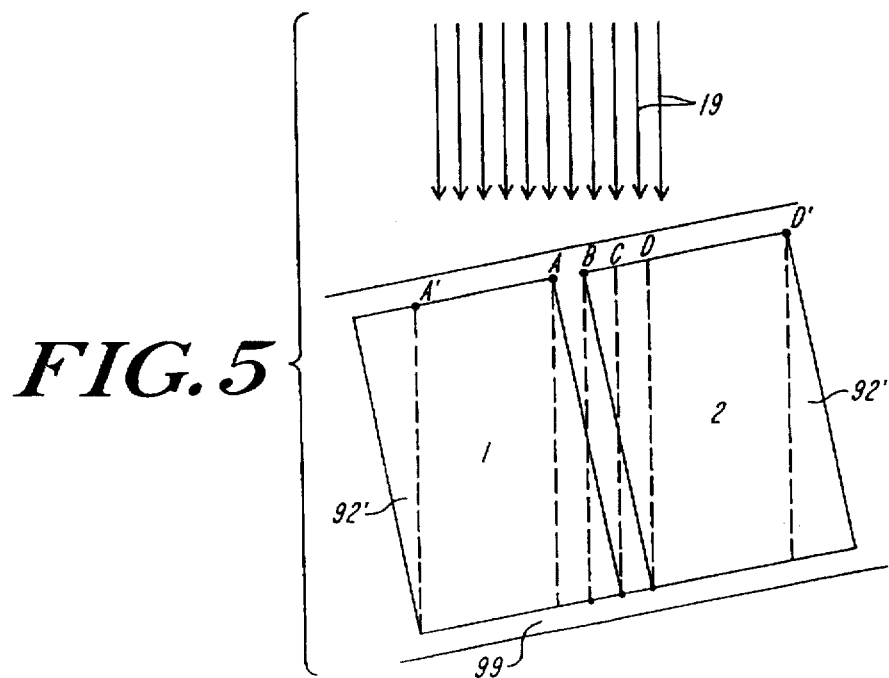
FIG. 5 is a simplified detail view of a portion of a detector array oriented at an angle with respect to radial lines extending from the focal spot.

FIG. 5 illustrates an enlarged view of two crystals in an array and the orientation of x-rays as they impinge on the crystals. Because the radial distance between the x-ray source and the detector assembly is relatively great (on the order of 850 mm), and the spaces between crystals in an array are relatively narrow (on the order of 0.2–0.3 mm), the rays 19 are essentially parallel. Approximately 90% of the radiation impinging on a detector crystal is absorbed in the first millimeter of penetration into the crystal. In a preferred embodiment, a detector crystal which provides approximately 2.5 millimeters of radiation penetration absorbs approximately 99.5% of the impinging radiation.

As a result of the angle at which the detector arrays are tilted, x-rays which impinge on detector 1 at point A or at points to the left of A and to the right of A' will be absorbed at approximately 99.5%. X-rays which impinge on detector 2 at point D or at points to the right of D and to the left of D' will also be absorbed at approximately 99.5%. X-rays which impinge on the region between points A and D will penetrate a portion of one or both detectors 1 and 2, depending on the angle of tilt and the point of impingement. Absorption will be approximately 90% for impingement between points B and C, and at intermediate amounts between about 90% and 99.5% for impingement in the regions AB and CD. The angle of tilt is selected so that the sum of the penetration depths of the radiation into the two adjacent crystals is sufficient for 90% absorption of the x-rays impinging in the region BC.

Adjacent detector modules are positioned at substantially the same radial distance from the focal spot, yet tilted at a preselected angle α with respect to a nominally perpendicular orientation, to obtain a tangentially overlapping, or "fish-scale", pattern of detector modules. The value of the angle will depend on the width of the space between detector crystals and on the radial height of the detector crystals, as illustrated in FIG. 5. It is preferred to have the detector arrays be tilted sufficiently to permit radiation to pass through about 1 millimeter of at least one detector crystal. This angle may, in practice, vary between about 7 and 11 degrees, although other angles may be necessary to achieve the desired penetration of radiation through at least a portion of at least one detector crystal.

An important benefit of the arrangement of the detector arrays according to the present invention is that the geometric efficiency of the CT scanner system is increased. A substantially continuous radiation detection zone is created by simply tilting the detector arrays with respect to a nominally perpendicular orientation relative to radial lines extending from the focal spot. This prevents alignment of the spaces between the detector crystals with x-rays emanating from the focal spot and ensures that the x-rays always penetrate at least a portion of a detector crystal and do not impinge solely on a space between detectors.

In a preferred embodiment of the invention, the anti-scatter plates 22 are positioned relative to the detectors 14 so that they are substantially aligned with the regions of constant maximum sensitivity of corresponding detectors. The number of anti-scatter plates need not equal the number of detectors and can be either greater or fewer than the number of detectors.

Figure 6:
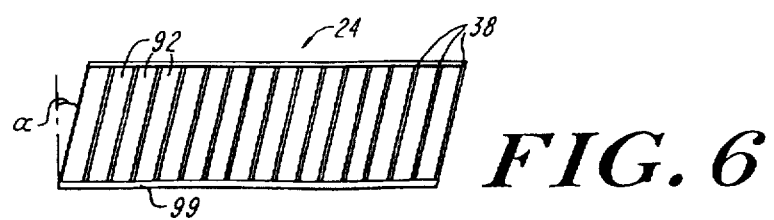
FIG. 6 is a simplified plan view of an alternate embodiment of the detector array.

Although the detector arrays have been shown as substantially rectangular elements with substantially rectangular individual detector channels, they can also be constructed to have the shape of a parallelogram, with individual detector channels 92' also being made in the shape of a parallelogram, as shown in FIG. 6. Such arrays could be positioned with the face of the array substantially perpendicular to radial lines 42 extending from the focal spot. The angle α of the crystals in the parallelogram configuration achieves the same result as the angle of tilt imparted to the arrays 24 in the embodiment of FIGS. 3 and 4.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An x-ray tomography scanning system of the type including (a) an x-ray source for defining a focal spot from which a beam of radiation is emitted, (b) means for supporting the x-ray source for rotation about a rotation axis, and (c) an x-ray detector assembly including a plurality of x-ray detectors cooperative with said x-ray source so as to define the beam of radiation from the focal spot to all of the detectors, said x-ray detector assembly including a plurality of detecting regions and non-detecting regions, said x-ray tomography scanning system further comprising:

means for fixedly positioning said detectors so that the detectors are always oriented relative to said focal spot and to one another so as to establish a substantially continuous radiation detection zone within said beam of radiation during a tomograhic scan, wherein substantially all radiation within said beam passing through said detector assembly always passes through a portion of at least one detecting region.

2. The x-ray tomography scanning system of claim 1, wherein said plurality of detecting regions includes a plurality detectors grouped in a plurality of substantially linear arrays, wherein the detector arrays are located at substantially the same radial distance from the focal spot and are oriented other than substantially perpendicular to radial lines extending from the focal spot.

3. The x-ray tomography scanning system of claim 2, wherein said detector arrays are positioned at a preselected angle α with respect to a nominally perpendicular orientation of said arrays relative to radial lines extending from the focal spot to approximately the centers of said arrays, at least some of said non-detecting regions including spaces between adjacent crystals of an array, wherein the spaces between adjacent detectors in an array are not aligned with x-rays emanating from the focal spot.

4. The x-ray tomography scanning system of claim 3, wherein each of said detecting regions includes a detector crystal for sensing said radiation, and wherein the absolute value of said angle α is a function of the height of the detector crystals and the width of the spaces between adjacent crystals in an array.

5. The x-ray tomography scanning system of claim 4, wherein the means for supporting the x-ray source for rotation about a rotation axis includes means for supporting both said x-ray source and said detector assembly for rotation about said rotation axis.

6. The x-ray tomography scanning system of claim 5, further comprising a gantry including a frame support, and the means for supporting said x-ray source and said detector assembly for rotation about said rotation axis includes a frame for supporting said x-ray source and said detector assembly for rotation in said frame support about said rotation axis.

7. The x-ray tomography scanning system of claim 6, wherein said frame includes a reference surface cooperative with said means for positioning said detectors.

8. The x-ray tomography scanning system of claim 7, further including an anti-scatter plate assembly including a plurality of anti-scatter plates disposed between the x-ray source and said detector assembly, and means for mounting said anti-scatter plate assembly relative to said detector assembly so that said anti-scatter plates are substantially aligned with radial lines extending from the focal spot, wherein the radiation detected by the detectors is substantially limited to radiation emitted directly from the x-ray source.

9. The x-ray tomography scanning system of claim 8, wherein said anti-scatter plates are substantially aligned with regions of substantially constant maximum sensitivity of corresponding detectors.

10. In a computed tomographic x-ray scanning system including (a) a gantry including a frame for rotatably supporting at least an x-ray source for rotation about a rotation axis, (b) an x-ray detector assembly including a plurality of x-ray detectors cooperative with said x-ray source and arranged in one or more substantially linear arrays, said x-ray detector assembly including a plurality of detecting regions and a plurality of non-detecting regions, (c) a support structure connected to said frame for supporting said detector assembly, and (d) an anti-scatter plate assembly mounted on said support structure, said anti-scatter plate assembly including a plurality of anti-scatter plates disposed between the x-ray source and said detector assembly, wherein said x-ray source defines a focal spot from which radiation is emitted and defines with the detector assembly a radiation beam, a method of establishing a substantially continuous radiation detection zone within the beam of radiation during a tomographic scan, the method comprising the step of:

fixedly positioning the detectors relative to the radiation beam so that substantially all radiation from said radiation beam passing through said detector assembly always passes through a portion of at least one detecting region.

11. The method of claim 10, wherein said detector arrays are located at substantially the same radial distance from the focal spot and are oriented other than substantially perpendicular to radial lines extending from the focal spot.

12. The method of claim 11, wherein said arrays are mounted on said support structure at a preselected angle α with respect to a nominally perpendicular orientation of said arrays relative to radial lines extending from the focal spot to approximately the centers of the arrays, at least some of said non-detecting regions including spaces between adjacent crystals of an array, wherein the spaces between adjacent detectors in an array are not aligned with x-rays emanating from the focal spot.

13. The method of claim 12, wherein each detecting region includes a detector crystal, and wherein the absolute value of said angle α is a function of the height of the detector crystals and the width of the spaces between adjacent crystals in an array.

\* \* \* \* \*